United States Patent [19]

Thuillier nee Nachmias et al.

[11] 4,255,585
[45] Mar. 10, 1981

[54] BENZOHETEROCYCLIC DERIVATIVES OF PHENOXYACETIC ACID

[75] Inventors: Germaine Thuillier nee Nachmias, Paris; Jacqueline S. Laforest nee Boutillier du Retail, Vincennes; Bernard J. M. Cariou, Combleux; Pierre A. R. Bessin, Chilly Mazarin; Jacqueline S. Bonnet nee Roux; Jean E. Thuillier, both of Paris, all of France

[73] Assignee: Centre European de Recherches Pharmacologique, Arcueil, France

[21] Appl. No.: 624,981

[22] Filed: Oct. 22, 1975

[51] Int. Cl.³ .................. C07D 333/24; C07D 307/77; A61K 31/38; A61K 31/34
[52] U.S. Cl. ........................................ 549/58; 549/51; 549/52; 549/54; 260/346.22; 424/275; 424/285

[58] Field of Search ................... 260/346.22, 332.2 A, 260/330.5; 549/51, 52, 54, 56, 58

[56] References Cited

U.S. PATENT DOCUMENTS

| | | | |
|---|---|---|---|
| 3,758,506 | 9/1973 | Godfroid | 260/332.2 A |
| 3,894,057 | 7/1975 | Effland | 260/346.2 R |
| 3,963,758 | 6/1976 | Pinhas et al. | 260/346.2 R |

OTHER PUBLICATIONS

Thuillier, "Chem. Abst.", vol. 83, (1975), p. 71707k.

*Primary Examiner*—Alan Siegel
*Attorney, Agent, or Firm*—Wegner & Bretschneider

[57] ABSTRACT

The present application relates to benzoheterocyclic derivatives of 2,3-dichlorophenoxyacetic acid, the preparation thereof and pharmaceutical compositions containing them.

10 Claims, No Drawings

BENZOHETEROCYCLIC DERIVATIVES OF PHENOXYACETIC ACID

BACKGROUND OF THE INVENTION

In recent years, various research efforts have been reported in the area of diuretic medicines.

In our U.S. Pat. No. 3,758,506 phenoxyacetic acid derivatives which are 4-(2-furyl-keto), (2-thienyl-keto) and [2-(5-methyl)-thienyl-keto]-2,3-dichlorophenoxyacetic acids and their salts have been described.

DESCRIPTION OF THE INVENTION

According to the present invention there is provided a phenoxy-acetic acid derivative of the general formula

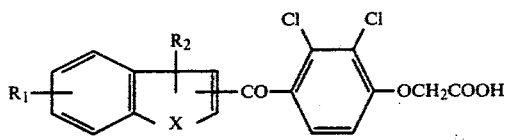

wherein X is oxygen or sulfur and $R_1$ and $R_2$, which are identical or different, are chosen in the group constituted by hydrogen atoms, halogen atoms and $C_{1-4}$ alkyl or alkoxy groups.

The preferred compounds of the invention are those in which X is 0 or S and $R_1$ and $R_2$ are H or Cl.

The salts of the compounds (alkalimetal salts and salts with pharmaceutically acceptable bases) are an object of the invention.

According to the invention, the compounds are prepared in the following way:
a benzoheterocyclic acid chloride is reacted with 2,3-dichloro-anisol in the conditions of Friedel-Crafts reaction in a solvent such as benzene, methylene chloride, carbon-disulfide, in the presence of a Lewis acid such as alumiminium chloride, to obtain a compound of formula II

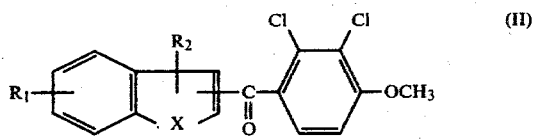

This compound is demethylated either by aluminium chloride in benzene or by melted pyridine hydrochloride. The phenol thus obtained is reacted either with a halogeno-acetic acid in a basic aqueous or alcoholic medium or with a halogeno-acetic ester in an alcoholic medium in the presence of an alkaline alcoholate. The compound of formula III is obtained

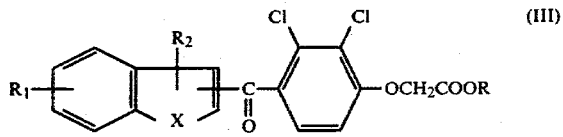

When R is an alkaline kation, compound III is treated with a hydrogen halide, and when R is an alkyl group, compound III is treated with an alkaline hydroxide in an aqueous alcoholic medium and then with a hydrogen halide to obtain a compound of formula I.

The salts of the acids of formula I are prepared by action of a pharmaceutically acceptable base in solvents such as alcohols, ketones. . . .

The following examples will serve to illustrate the invention.

EXAMPLE 1

4-(2-benzofuryl-keto)-2,3-dichloro-phenoxyacetic acid (a) 14 g (0.1 mole) of aluminium chloride are introduced little by little in a solution of 16 g (0.09 mole) of 2,3-dichloro-anisol and 16 g (0.09 mole) of 2-benzofuran-carboxylic acid chloride in 200 ml of methylene chloride the mixture is taken up to reflux for 4 hours, then poured on crushed ice (300 g) and concentrated hydrochloric acid (10 ml); the precipitate is filtered off, washed with an aqueous solution of sodium hydroxide (10 N), then with water and dried. 22 g of 2-benzofuryl (2,3-dichloro-4-methoxy-phenyl) ketone are obtained. Melting point 148° C. after crystallization from ethylacetate.

(b) 18 g (0.056 mole) of the methyl ether previously obtained are dissolved in 200 ml of benzene and 15 g (0.112 mole) of aluminium chloride are introduced into the solution. The mixture is taken up to reflux temperature for 4 hours, then poured into aqueous hydrochloric acid (200 ml). The precipitate is filtered off and purified by dissolving in an aqueous sodium hydroxide solution and precipitating in acid medium. 17 g of 2-benzofuryl (2,3-dichloro-4-hydroxy-phenyl) ketone are obtained. Melting point 163° C. after crystallization from xylene.

(c) 16 g (0.05 mole) of the phenol previously obtained are introduced into a sodium ethylate solution (1.15 g of sodium in 150 ml of ethanol) and then, after 15 mn of reflux, 7.35 g (0.06 mole) of chloracetic acid ethylester. The mixture is kept boiling for 6 hours and then, after hot filtration, the solvent is evaporated under reduced pressure. The residue is washed with an aqueous basic solution, with water and dried. After crystallization from ethanol, 14 g of 4-(2-benzofuryl-keto)-2,3-dichlorophenoxyacetic acid ethylester is obtained. Melting point 82° C.

(d) 10.2 g (0.026 mole) of the ester obtained are dissolved in ethanol, and 26 ml of an aqueous solution of sodium hydroxide N are added. The mixture is kept 2 hours boiling. The precipitate is dissolved in hot water and the solution acidified with hydrochloric acid. The solid formed is dried and crystallized from acetone (95%). 7 g of 4-(2-benzofuryl-keto)-2,3-dichloro-phenoxyacetic acid is obtained. Melting point 253° C.

EXAMPLE 2

4-(2-benzothienyl-keto)-2,3-dichloro-phenoxyacetic acid.

The following products are obtained according to the process described in Example 1.

(a) 2-benzothienyl (2,3-dichloro-4-methoxy-phenyl)ketone; Melting point = 170° C.

(b) 2-benzothienyl (2,3-dichloro-4-hydroxy-phenyl)ketone; Melting point = 186° C.

(c) ethyl 4-(2-benzothienyl-keto)-2,3-dichloro-phenoxyacetate; Melting point = 101° C.

(d) 4-(2-benzothienyl-keto)-2,3-dichloro-phenoxyacetic acid; Melting point = 236° C.

The sodium salt of the acid is prepared by reacting the acid and the sodium hydroxide in equimolar proportions, in ethanol. Melting point > 300° C.

The piperazine salt of the acid is prepared by reacting 1 mole of piperazine with 2 moles of acid in ethanol. Melting point = 200° C.

EXAMPLE 3

4-[2-(3-chloro)-benzothienyl-keto]-2,3-dichloro-phenoxy acetic acid.

The following products are obtained according to the process described in Example 1 or 2.

(a) [2-(3-chloro)-benzothienyl](2,3-dichloro-4-methoxy-phenyl)ketone; Melting point = 155° C.
(b) [2-(3-chloro)-benzothienyl](2,3-dichloro-4-hydroxy-phenyl)ketone; melting point = 186° C.
(c) ethyl 4-[2-(3-chloro)-benzothienyl-keto]-2,3-dichlorophenoxy acetate.
(d) 4-[2-(3-chloro)-benzothienyl-keto]-2,3-dichloro-phenoxyacetic acid; melting point = 202° C.

Potassium salt Melting point = 274° C.
Piperazine salt Melting point = 212° C. (hydrate).

The compounds of the invention have diuretic, hypotensive and uricosuric acitivity as demonstrated in various pharmacological procedures. More specifically, the compounds of the above Examples, have been tested in different pharmacological experiments and compared to three well known substances: ethacrynic acid, furosemide and benziodarone.

Acute toxicity

The three compounds were administered in the usual way to lots of 10 male mice (Swiss C.D.) of average weight 20 g. Mortality was assessed after 48 hours for toxicity per os. The results are given in Table I.

| Compound | LD 50 per os mg/kg |
|---|---|
| Example 1 | LD 50 < 1000 |
| Example 2 | MLD > 1000 |
| Example 3 | LD 50 > 1000 |
| ethacrynic acid | 600 |
| furosemide | 1125 |

Diuretic activity

The three compounds were administered to Male Swiss C.D. mice of average weight 22 g. The animals were deprived of food and drink for 2 hours prior to treatment.

The animals were grouped two by two in cages where their metabolism is to be monitored. Sampling of the urine 2 and 4 hours after treatment. The experiments were made per lot of six pairs. The products were administered at constant volume.

The following determinations were made:
volume of urine excreted
Na+ and K+ ions expressed in milliequivalents (Milli-val or M. Eq.) excreted in 2 or 4 hours (Eppendorf Flame Photometer);
uric acid excreted expressed in mg/2 or 4 hours determined by Caraway's method (Amer. J. Clin. Pathol. 1955. 25 840).

The results are given in Table II. They are considered in the form of the coefficient:

$$\frac{\text{mean value for the treated animals}}{\text{mean value for the controls}}$$

TABLE II

| Compound | Diuresis | Na+ | K+ | Na+/K+ | Uricosuria |
|---|---|---|---|---|---|
| Example 1* | 1.3 | 1.52 | 1.74 | 0.87 | 1.56 |
| Example 2* | 1.2 | 1.18 | 0.91 | 1.29 | 1.05 |
| Example 3* | 1.3 | 1.29 | 1.17 | 1.10 | 1.26 |
| ethacrynic acid** | 2.4 | 2.76 | 1.48 | 1.87 | 1.27 |
| furosemide** | 3.0 | 4.28 | 1.51 | 2.83 | 1.34 |
| benziodarone** | | | | | 1.44 |

*administered dosis = 100 mg/kg P.O.
**administered dosis = 20 mg/kg P.O.

The compounds of the invention and their salts are useful in human and veterinary therapy as diuretics, hypotensives and uricosurics.

These compounds can be used as active principles associated or not with other appropriate active principles, in the principal pharmaceutically suitable forms, such as tablets, capsules, suppositories and injectable solutions.

For per os administration, for suppositories, and for injectable solutions the dose can be from 0.050 to 1 g of active product.

The compounds can be administered in daily doses varying from 100 to 1500 mg at these doses, they do not provoke any undesirable secondary phenomena; in particular, potassium loss is relatively weak.

An example of typical formulation is as follows:

| FORMULATION 1. - FOR TABLETS | |
|---|---|
| | G |
| Active principle | 0.500 |
| Potato starch | 0.020 |
| Polyvinyl pyrrolidone | 0.020 |
| Maize starch | 0.045 |
| Talc | 0.020 |
| Magnesium stearate | 0.015 |

By substituting the appropriate starting materials and employing the procedures of Examples 1, 2 and 3 the following compounds of Formula I are prepared: 4-[2-(3-methyl)-benzofuryl-keto]-2,3-dichloro-phenoxyacetic acid; 4-[2-(5-methoxy)-benzothienyl-keto]-2,3-dichloro-phenoxy-acetic acid; 4-(3-benzothienyl-keto)-2,3-dichloro-phenoxy-acetic acid.

We claim:

1. A phenoxyacetic acid selected from the group consisting of a phenoxy-acetic-acid of the general formula

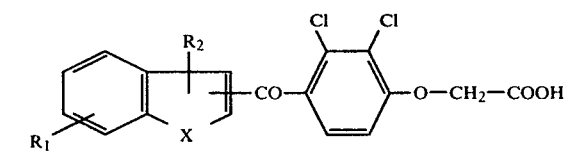

wherein X is oxygen or sulfur and $R_1$ and $R_2$, which are identical or different, are selected from the group consisting of hydrogen, halogen, $C_{1-4}$ alkyl and alkoxy, alkalimetal salts of a said acid or addition salts of said acid with a pharmaceutically acceptable base.

2. A phenoxyacetic acid according to claim 1, having the general formula

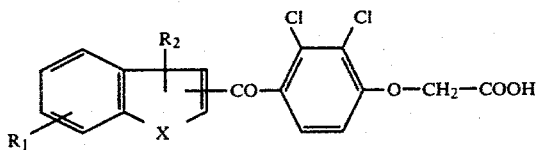

wherein X is O or S and $R_1$ and $R_2$ which are identical or different, are H or Cl.

3. A compound selected from the group consisting of 4-(2-benzothienyl-keto)-2,3-dichloro-phenoxy-acetic acid, alkalimetal salts thereof and addition salts thereof with a pharmaceutically acceptable base.

4. A compound selected from the group consisting of 4-[2-(3-chloro)-benzothienyl-keto]-2,3-dichloro-phenoxy-acetic acid, alkalimetal salts thereof and addition salts thereof with a pharmaceutically acceptable base.

5. A compound selected from the group consisting of 4-(2-benzofuryl-keto)-2,3-dichloro-phenoxy-acetic acid, alkalimetal salts thereof and addition salts thereof with a pharmaceutically acceptable base.

6. 4-(2-benzofuryl-keto)-2,3-dichloro-phenoxy-acetic acid.

7. A phenoxyacetic acid according to claim 1 wherein X is oxygen.

8. A phenoxyacetic acid according to claim 1 wherein X is sulfur.

9. A phenoxyacetic acid according to claim 2 wherein X is oxygen.

10. A phenoxyacetic acid according to claim 2 wherein X is sulfur.

* * * * *